United States Patent [19]

Juneja et al.

[11] Patent Number: 6,136,302
[45] Date of Patent: Oct. 24, 2000

[54] PROCESS OF MAKING ZIRCONIUM-ALUMINUM ANTIPERSPIRANTACTIVE

[75] Inventors: Prem Sagar Juneja; David Frederick Swaile, both of Cincinnati, Ohio

[73] Assignee: The Procter & Gamble Company, Cincinnati, Ohio

[21] Appl. No.: 09/252,385

[22] Filed: Feb. 18, 1999

[51] Int. Cl.$^7$ .............................. A61K 7/32; A61K 7/34; A61K 7/38; A61K 7/00
[52] U.S. Cl. ................................ 424/65; 424/66; 424/68; 424/400; 424/401; 423/463
[58] Field of Search .................................. 424/65, 66, 68, 424/400, 401; 423/463

[56] References Cited

U.S. PATENT DOCUMENTS

| | | | |
|---|---|---|---|
| 3,903,258 | 9/1975 | Siegal | 424/66 |
| 3,981,986 | 9/1976 | Rubino | 424/47 |
| 4,223,010 | 9/1980 | Rubino et al. | 424/66 |
| 4,871,525 | 10/1989 | Giovanniello et al. | 423/463 |

FOREIGN PATENT DOCUMENTS

| | | |
|---|---|---|
| 0 499 456 A2 | 8/1992 | European Pat. Off. . |
| 2 076 289 | 12/1981 | United Kingdom . |
| WO 92/04281 | 3/1992 | WIPO . |

*Primary Examiner*—Shelley A. Dodson
*Attorney, Agent, or Firm*—William J. Winter

[57] ABSTRACT

Disclosed is a process for making zirconium-aluminum salts for use as antiperspirant active, which process comprises the step of anhydrous mixing of a zirconium salt and an aluminum salt to form a zirconium-aluminum salt, wherein the mixture of zirconium and aluminum salts is substantially free of unbound water at all times during the process. The zirconium, aluminum and zirconium-aluminum salts in the process are in the form of particulate or other solids, or can otherwise be dissolved or dispersed in a non-aqueous medium. The process allows for the formation of zirconium-aluminum salts as antiperspirant active without relying upon prior art methods which teach that zirconium-aluminum salts require reaction together in an aqueous medium. This process is more stable than the prior art methods and provides better control over optimizing the polymer size distribution within the resulting zirconium-aluminum salts.

25 Claims, 1 Drawing Sheet

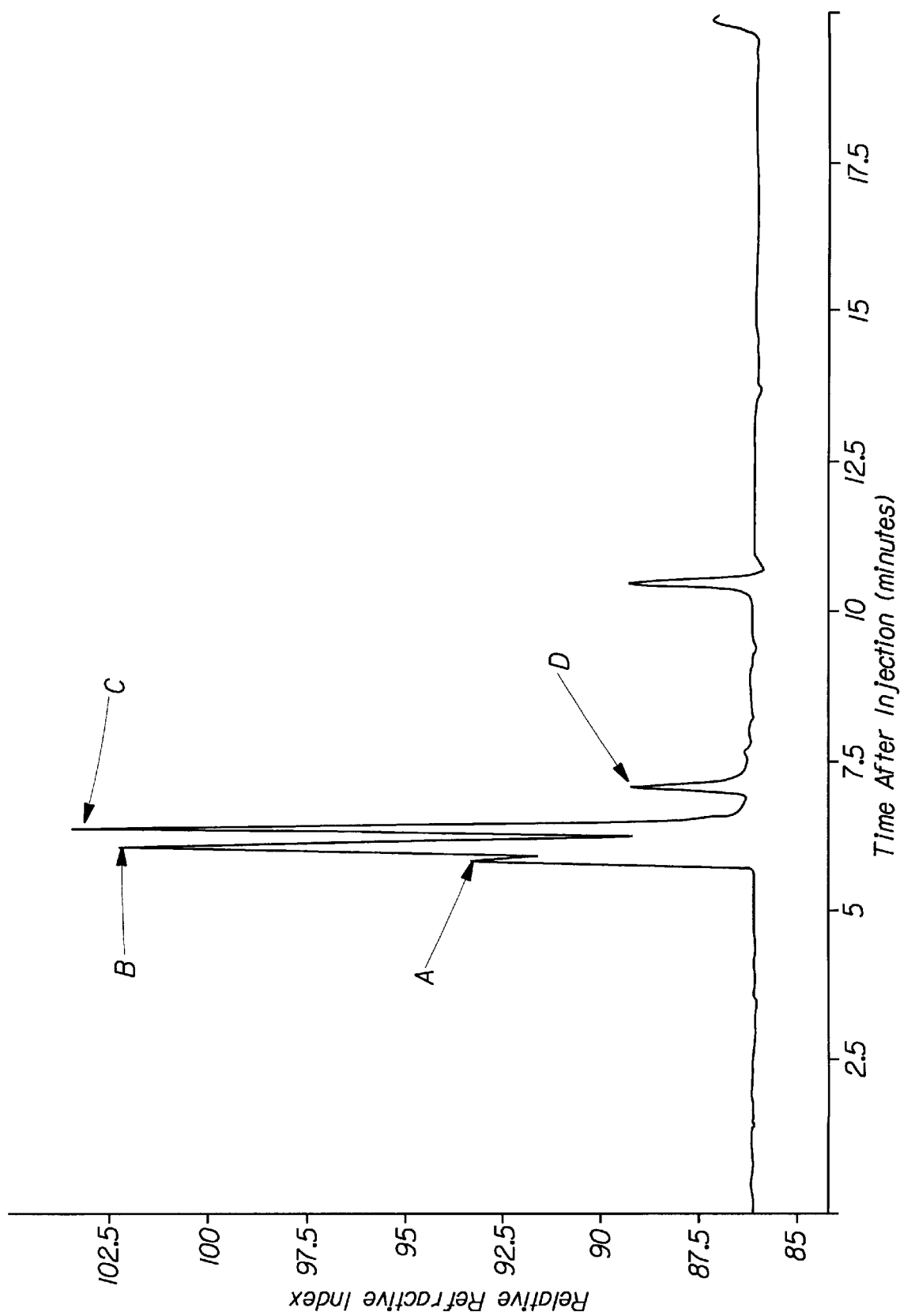

PROCESS OF MAKING ZIRCONIUM-ALUMINUM ANTIPERSPIRANT ACTIVE

FIELD OF THE INVENTION

The present invention relates to an anhydrous mixing process for making a zirconium-aluminum antiperspirant active.

BACKGROUND OF THE INVENTION

There are many types of topical antiperspirant products that are commercially available or otherwise known in the antiperspirant art. These products typically contain an antiperspirant active in the form of an aluminum and/or zirconium salt, and the majority of these products contain a combination of aluminum and zirconium salts as the antiperspirant active.

These combinations of aluminum and zirconium salts for use as antiperspirant active comprise aluminum and zirconium hydrolysis polymers formed by the partial neutralization of acidic aluminum ($Al+3$) and zirconium ($Zr+4$) metal ions. These active materials are most typically made by mixing basic zirconium salts (e.g., zirconium hydroxy chloride) and basic aluminum salts (e.g., aluminum chlorohydrate) in an aqueous solution and then spraying dry the aqueous solution to produce a solid zirconium-aluminum salt. This type of process generally requires the use of a buffer such as glycine to prevent precipitation of the salts during the aqueous mixing process.

Recent methods for making zirconium-aluminum salts have been directed to the formation of those zirconium-aluminum salts having enhanced antiperspirant activity. Such methods typically involve heating a solution of an aluminum salt and a zirconium salt to allow the salts to react while in solution to form a new zirconium-aluminum salt comprising smaller and more effective aluminum hydrolysis polymers. When the desired polymer size distribution is achieved during the mixing and heating process, the heated mixture is typically spray dried to form a solid zirconium-aluminum salt having improved antiperspirant activity.

There are many different methods described in the art for making zirconium-aluminum salts. The antiperspirant art teaches that most or all of these methods must involve at least one process step in which aluminum salts and zirconium salts are mixed together in an aqueous solution to allow the two salts to react and form a zirconium-aluminum salt comprising an aluminum polymer distribution suitable for use as an antiperspirant active.

An example of one such method is described in U.S. Pat. No. 5,589,196 (Callaghan et al.) which teaches a process in which zirconium and aluminum salts are mixed together in an aqueous solution, subjected to heating to form the desired aluminum polymer distribution, and then rapidly dried to capture the polymer distribution achieved and to produce a dry, stable zirconium-aluminum salt. This process is directed to optimizing aluminum chemistry by shifting the aluminum polymer distribution in the final zirconium-aluminum salt toward smaller molecular weight, more effective, aluminum polymers.

Another similar method for making zirconium-aluminum salts is described in EP653203 (Rosenberg et al.) which teaches a process of making zirconium-aluminum salts by forming an aqueous mixture of a zirconium salt and glycine at ambient temperatures, combining the aqueous mixture with an aluminum chlorohydrate starting material, and rapidly drying the resulting aqueous mixture to form a zirconium-aluminum glycine complex. Rosenberg et al. teaches that an aqueous mixture of zirconium and aluminum salts is essential to forming the desired zirconium-aluminum glycine complex, but that the residence time for the zirconium and aluminum while together in solution should be minimized.

It is therefore generally taught in the antiperspirant art that zirconium-aluminum salts can only be formed by interacting various aluminum and zirconium materials together in an aqueous mixture. These aqueous mixtures, however, are not particularly stable during processing or formulation in that the aluminum and zirconium polymer distribution tends to shift when subjected to heat or if allowed to set or age for even a short period of time. To stabilize the polymer distribution, these aqueous mixtures are dried or otherwise dehydrated to form a more stable material that is substantially free of unbound water.

It has now been found that zirconium-aluminum salts can be made without relying upon as a process intermediate an aqueous solution containing a zirconium salt and an aluminum salt. Contrary to the historical teaching in the antiperspirant art, it has now been found that aluminum salts can be mixed with zirconium salts to form a zirconium-aluminum salt for use as an antiperspirant active, without involving any intermediate process step which combines the zirconium salt and the aluminum salt together in an aqueous solution. It has been found that the anhydrous process itself can result in the same zirconium-aluminum polymer distributions that were once believed to be made only from the reaction of zirconium and aluminum salts together in an aqueous medium.

It is therefore an object of the present invention to provide a new process for making zirconium-aluminum salts for use as antiperspirant active, without reliance upon the prior art methods which teach the use of aqueous solutions containing zirconium and aluminum materials together. It is a further object of the present invention to provide such a process by anhydrous mixing of aluminum salts and zirconium salts together to form the zirconium-aluminum polymer described in the art, wherein the anhydrous process never involves any aqueous mixture containing both aluminum and zirconium salts.

SUMMARY OF THE INVENTION

The present invention is directed to a process for making zirconium-aluminum salts for use as antiperspirant actives, which process comprises the step of anhydrous mixing of a zirconium salt and aluminum salt to form a solid zirconium-aluminum salt, wherein the aluminum salt prior to the anhydrous mixing step is preferably substantially free of zirconium and the zirconium salt prior to the anhydrous step is preferably substantially free of aluminum, and wherein the process does not include any intermediate process step in which aluminum and zirconium salts are combined or otherwise used together in an aqueous medium.

It has been found that the anhydrous mixing process of the present invention allows for the formation of zirconium-aluminum salts effective for use as antiperspirant active. Execution of the anhydrous process specifically excludes the use of any intermediate process step involving the combination of zirconium and aluminum salts in an aqueous medium. The anhydrous mixing process is more stable than the prior art methods involving the use of aqueous mediums containing both zirconium and aluminum salts. It is also easier to control the desired zirconium-aluminum polymer distribution by the anhydrous mixing as compared to the historical aqueous solution methods.

BRIEF DESCRIPTION OF THE DRAWING

FIG. 1 is an example of chromatogram for a zirconium-aluminum salt made in accordance with process of the present invention. The chromatogram is also generated in accordance with the gel permeation chromatography (GPC) methodology described herein. The vertical axis represents relative refractive indices. The horizontal axis represents the duration of time (minutes) required for the different polymer species of a zirconium-aluminum salt to pass through the GPC column. Peaks I–II are represented as a single spike at about 5.84 minutes (A); Peaks III, IV and V are represented at about 6.09 minutes (B), 6.39 minutes (C) and 7.08 minutes (D), respectively. Peaks I–II correspond to co-eluting aluminum and zirconium polymer species; Peaks III, IV and V correspond to other aluminum polymer species in the injected sample. The unidentified peak at the far right of the chromatogram is a halogen peak associated with the salt sample.

DETAILED DESCRIPTION OF THE INVENTION

The process of the present invention is directed to a method of making zirconium-aluminum salts as antiperspirant actives, wherein an aluminum salt is combined with a zirconium salt to form a zirconium-aluminum salt suitable for topical application to the skin as an antiperspirant active.

The phrase "anhydrous mixing" as used herein refers to the process of the present invention and the antiperspirant active made in accordance with that process, wherein aluminum and zirconium salts are combined and mixed together as solids or within non-aqueous mediums to form a zirconium-aluminum salt that is likewise in solid form or within a non-aqueous medium, and wherein the process specifically excludes any intermediate step involving an aqueous medium containing a combination of aluminum and zirconium salts.

The term "non-aqueous medium" as used herein refers to the solid or liquid vehicle in which the aluminum, zirconium or zirconium-aluminum salts for use in the process of the present invention are maintained, wherein the "non-aqueous medium" contains less than 25%, preferably less than about 10%, more preferably less than about 5%, even more preferably less than 3%, most preferably zero percent, by weight of unbound water.

The term "aqueous medium" as used herein refers to any solid or liquid medium other than the non-aqueous mediums as defined herein, and will typically mean any medium containing at least 25% by weight of unbound water.

The term "zirconium-aluminum salt" as used herein refers to the combination of zirconium salts and aluminum salts made in accordance with the process herein, wherein each of the zirconium and aluminum salts combine to form zirconium and aluminum hydrolysis polymers, respectively.

The process of the present invention, and the compositions related to or resulting therefrom, can comprise, consist of, or consist essentially of the essential elements and limitations of the invention described herein, as well as any of the additional or optional ingredients, components, or limitations also described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

I. Process

The process of the present invention comprises the anhydrous mixing of a zirconium salt and an aluminum salt to form a zirconium-aluminum active in solid form or contained within a non-aqueous medium, wherein the process specifically excludes any intermediate or other process step involving the combination of the zirconium and aluminum salts in an aqueous medium. Preferably, the aluminum salt prior to the anhydrous mixing step is substantially free of zirconium, and the zirconium salt prior to the anhydrous mixing step is substantially free of aluminum. In this context, the term substantially free means that the identified active salt contains less than 25%, preferably less than 5%, preferably zero percent, by weight of the other active salt.

The term "anhydrous mixing" as used herein means that the zirconium and aluminum salts are combined in accordance with the process of the present invention, without the use of or reliance upon any process step in which the aluminum and zirconium salts are combined or otherwise together in an aqueous medium. The salts for use in the anhydrous process may be in the form of particulate or other solid form or as dissolved or suspended solids in a non-aqueous medium. The zirconium and aluminum salts for use in the process can and typically will contain minor amounts of bound water of hydration, e.g., from zero to about 25% of water by weight of the active, preferably from about 3% to about 20% of water by weight of the active.

Aluminum salts for use in the process of the present invention can be any aluminum salt that is known or otherwise effective for use in developing zirconium-aluminum antiperspirant active. The aluminum salt includes inorganic and organic salts of aluminum as well as mixtures of such salts. Preferred are salts or salts derived from aluminum halides, aluminum chlorohydrate, aluminum hydroxyhalides and mixtures thereof, and include aluminum salts which conform to the formula:

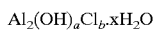

$$Al_2(OH)_aCl_b \cdot xH_2O$$

wherein a is from about 0 to about 5; the sum of a and b is about 6; x is from about 1 to about 6; and wherein a, b, and x may have non-integer values. Particularly preferred are the aluminum chlorhydroxides referred to as "⅚ basic chlorhydroxide", wherein a=5, and "⅔ basic chlorhydroxide", wherein a=4. The aluminum salts may be prepared by any method known or otherwise effective in making such aluminum salts as antiperspirant active materials. Nonlimiting examples of aluminum salts and processes for making them are described in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, which descriptions are incorporated herein by reference.

Zirconium salts for use in the process of the present invention can be any zirconium salt that is known or otherwise effective for use in developing zirconium-aluminum antiperspirant actives. The zirconium salts include inorganic and organic salts of zirconium as well as mixtures of such salts, and includes those zirconium salts which conform to the formula:

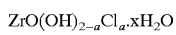

$$ZrO(OH)_{2-a}Cl_a \cdot xH_2O$$

wherein a is from about 1.0 to about 2.0; x is from about 1 to about 7; and wherein a and x may both have non-integer values. Preferred are zirconyl oxyhalides, zirconyl hydroxyhalides, and combinations thereof. The zirconium salts may be prepared by any method known or otherwise effective in making such zirconium salts as antiperspirant active materials. Nonlimiting examples of zirconium salts and processes for making them are disclosed in described in Belgian Patent 825,146, Schmitz, issued Aug. 4, 1975 and U.S. Pat. No. 4,223,010 (Rubino), which descriptions are incorporated herein by reference.

The aluminum salt for use in the process of the present invention is preferably prepared by methods well known for making aluminum salts which have improved antiperspirant efficacy. These improved aluminum actives can be made by any of a variety of methods well known in the antiperspirant art for making improved aluminum active, which will typically involve the application of heat to a dilute aqueous solution of an aluminum salt (e.g., less than 20% of an aluminum salt by weight of the dilute solution) to form a solid aluminum salt comprising aluminum hydrolysis polymers having a lower average molecular weight, or a higher concentration of lower average molecular weight polymers, and therefore an improved antiperspirant efficacy. Examples of such methods are described in U.S. Pat. No. 4,871,525 (Giovanniello et al.) and U.S. Pat. No. 4,359,456 (Gosling et al.), which patents are incorporated herein by reference.

The anhydrous mixing process of the present invention requires that the aluminum and zirconium salts are blended together as non-aqueous fractions, preferably as flowable solid particulates, wherein the non-aqueous fractions are not blended or otherwise together at any time during the blending process in an aqueous medium, but can otherwise be blended together by any known or otherwise effective technique for blending together dry solids or other anhydrous materials. For solid particulates, the blending can take place in any suitable container or space that can provide for anhydrous mixing of such materials, e.g., rotating drum, stationary vessel with blending means, spray mixing tower, etc. The blending is typically continued until the two solid fractions are homogeneously blended together to the extent desired.

The resulting anhydrous mixture comprises zirconium-aluminum salts as defined herein, which anhydrous mixture preferably has an aluminum to zirconium atomic ratio of from about 1:1 to about 10:1, more preferably from about 2:1 to about 8:1, and a metal salt to halogen weight ratio (e.g., Al+Zr)/Cl) of from about 0.9:1 to 2.1:1, more preferably from about 1.2:1 to about 1.7:1.

The zirconium-aluminum salt in the anhydrous mixture is preferably in the form of a zirconium-aluminum hydroxy halide complex comprising a neutral-amino-acid such as glycine or a polyhydric alcohol such as propylene glycol or polyethylene glycol, preferably a glycine complex such as zirconium-aluminum hydroxy halide glycinate, wherein the zirconium to neutral-amino-acid ratio is from about 0.25:1 to about 5:1, preferably from about 0.5:1 to about 2:1. The neutral amino acid or polyhydric alcohol can be added to either the zirconium salt and/or the aluminum salt prior to the anhydrous mixing process, and is preferably added to at least the non-aqueous zirconium fraction prior to the blending process. Adding of these materials to either of the individual salts results in the formation of an aluminum and/or zirconium salt complexed to the added material which then helps prevent precipitation or gellation of the acidic and basic salts in the blend.

The anhydrous mixture resulting from the process herein can be in the form of a particulate or other solid form, or it can be in the form of dissolved or suspended salts in a non-aqueous medium. Preferred are anhydrous mixtures in the form of flowable particulates. The particle size of the preferred particulates is preferably less than about 20 microns, more preferably less than about 4 microns, even more preferably from about 0.1 to about 2 microns. The average particle size can be controlled by 1) using solid aluminum and/or zirconium particulate salts prior to and during the anhydrous process which have the desired average particle size, 2) using an anhydrous mixing step involving particulate solids with sufficient application of shear to reduce average particle size during the blending process, and/or 3) by reducing particle size of the resulting anhydrous blend by any known or otherwise effective particle size reduction method. Nonlimiting examples of suitable particle size reduction methods include grinding or the application of other suitable shear force to the preferred zirconium-aluminum salt particulates.

The anhydrous mixing process of the present invention can therefore comprise a variety of blending variations, provided that the aluminum and zirconium salts are not mixed together or otherwise combined in an aqueous medium at any time during the process. Variations of the process include the mixing together of the aluminum and zirconium salts as solids or dissolved solids, wherein one or both of the dissolved or solid salt forms are provided for use in the process in a solid, semi-solid, and/or liquid nonaqueous medium. The process includes the mixing together of the active salts as solids with solids, solids with liquids, liquids with liquids, liquids with semi-solids, and so forth. One or both of the aluminum and zirconium salts can be derived from aqueous or nonaqueous mediums, provided that the aluminum and zirconium salts are not allowed to mix or otherwise combine together in an aqueous medium during the process herein.

The anhydrous mixing process of the present invention preferably involves the use of a buffering material, more preferably an amino acid buffer. This buffering material can be used in the process of making either the zirconium salt and/or solid aluminum salt, but is preferably used in at least the formation of the solid zirconium salt. Suitable buffers include salts of neutral amino acids, examples of which include glycine (including alkaline and alkaline earth glycinates and magnesium hydroxy glycinates), DL-valine, DL-alanine, arginine, L-proline, and combinations thereof. Most preferred is glycine.

The aluminum and/or zirconium salts for use in the process can be prepared by various methods including those involving aqueous solutions. If aqueous solution preparation is used to obtain these materials, substantially all unbound water should be removed from the material prior to its use in the anhydrous mixing process of the present invention.

The non-aqueous mediums suitable for use in the process include any known or otherwise effective vehicle for topical application from an antiperspirant and deodorant composition, and which is substantially free of water as described herein. Nonlimiting examples of such vehicles are described in U.S. Pat. No. 5,840,288 (Guskey et al.), U.S. Pat. No. 5,871,717 (Bretzler et al.) and U.S. Pat. No. 5,585,092 (Trandai et al.), which descriptions are incorporated herein by reference.

II. Methodology

The zirconium-aluminum salts made in accordance with the anhydrous mixing process of the present invention can have a polymer size distribution similar to the polymer size distribution of the zirconium-aluminum salts made by the prior art aqueous solution methods. Polymer size distribution of the resulting anhydrous mix can be defined by the size exclusion chromatography method as described hereinafter using Gel Permeation Chromatography (GPC).

Solid zirconium-aluminum salts made in accordance with the anhydrous mixing process of the present invention are dissolved in 0.01M nitric acid and chromatographed using 5 $\mu$l injections in a series of three consecutive Waters $\mu$ Porasil Columns, 3.9×300 mm, 10 $\mu$m packing. For non-aqueous suspension or solutions of zirconium-aluminum active in a water-soluble non-aqueous medium, such should be treated in the same manner as solid active salts as described above. For non-aqueous suspensions of such salts in a water-insoluble non-aqueous medium, the suspended active should be extracted into the 0.01M nitric acid, and only the resulting nitric acid solution injected onto the column. Chromatograms are visualized using a Waters 410 Differential Refractometer. Samples are prepared immediately prior to analysis to prevent degradation. Relative peak areas and area ratios are calculated using a Waters Millennium Data System (Version 2.10 or equivalent). The peaks observed in the chromatogram are designated in order of appearance on the chromatogram as Peaks I–II (appears as a single peak) and Peaks III, IV and V (see FIG. 1). The area of Peaks III, IV and V correspond to the relative concentration of aluminum polymer species exiting the column during the specified time period from the injected sample. The area of Peaks I–II correspond to the relative concentration of co-eluting aluminum and zirconium polymer species appearing initially on the chromatogram.

Prior to any analysis, the columns should be conditioned individually by repeated 100 $\mu$l injections of a 10% zirconium-aluminum trichlorohydrate glycine solution (containing at least 10% zirconium on a solid basis). Conditioning is complete when the area percent of Peaks I–II become relatively constant. During the conditioning process, the area percent of Peaks I–II will increase, and there will be reduction in retention for all peaks. Columns should be discarded when Peaks I and II are no longer resolved from Peak III.

It has been found that the zirconium-aluminum salt made in accordance with the anhydrous mixing process herein can have a polymer size distribution as characterized by the GPC methodology herein that is the same or similar to that found in zirconium-aluminum salts made by prior art aqueous solution methods. The zirconium-aluminum salts made in accordance with the process of the present invention will typically have an average ratio of the area of Peak IV to Peak III as defined by the methodology herein of at least about 0.1:1, preferably from about 0.2:1 to about 1.4:1.

III. Antiperspirant and Deodorant Compositions

The antiperspirant and deodorant compositions of the present invention comprise the antiperspirant active made in accordance with the anhydrous mixing process of the present invention. The concentration of the active in such compositions should be sufficient to provide the desired antiperspirant and/or deodorant efficacy, and will typically range from about 0.1% to about 60%, more typically from about 0.5% to about 30%, preferably from about 5% to about 26% by weight of the composition. The antiperspirant active, when formulated into the composition, may be solubilized or in the form of dispersed solids, preferably in the form of dispersed solids.

The antiperspirant and deodorant compositions of the present invention may further comprise other antiperspirant and/or deodorant actives, but are preferably substantially free of zirconium-aluminum salts made by mixing zirconium and aluminum salts together in an aqueous solution prior to forming the solid or solubilized zirconium-aluminum active in the composition. In this context, the term "substantially free" means that the composition preferably contains less than about 5%, more preferably less than about 1%, even more preferably zero percent, by weight of such zirconium-aluminum active materials.

The antiperspirant and deodorant compositions of the present invention are preferably anhydrous. In this context, the term anhydrous means that the compositions preferably contain less than about 5%, more preferably less than 2%, even more preferably less than 0.1%, most preferably zero percent, by weight of water other than water of hydration bound to the antiperspirant active or other material in the composition.

The antiperspirant and deodorant compositions of the present invention may further comprise any material known or otherwise suitable for use in topical antiperspirant and deodorant compositions, nonlimiting examples of which include solid or liquid carriers, surfactants or other wash-off aids, deodorant actives (e.g., antimicrobials, adsorbents, deodorant perfumes), fragrances, chelating agents, residue masking agents, other skin active agents, moisturizers or emollients, inert solids such as talc or solid polyethylene, preservatives, processing aids, dyes or other colorants, or suspending agents.

The antiperspirant and deodorant compositions of the present invention may be formulated into any solid, semi-solid or liquid product form suitable for topical application to the underarm or other area of the skin where application is desired. Nonlimiting examples of suitable product forms include gel or wax sticks, soft solids or creams, roll-ons, and aerosol or pump sprays.

Nonlimiting examples of suitable optional materials and product forms are described in U.S. Pat. No. 5,156,834 (Beckmeyer et al.); U.S. Pat. No. 5,718,890 (Putman et al.); U.S. Pat. No. 5,429,816 (Hofrichter et al.); U.S. Pat. No. 5,744,130 (Guskey et al.); U.S. Pat. No. 5,605,681 (Trandai et al.); U.S. Pat. No. 5,298,236 (Orr et al.); U.S. Pat. No. 4,985,238 (Tanner et al.); and U.S. Pat. No. 4,904,463 (Johnson et al.), which descriptions are incorporated herein by reference.

IV. Method of Use

The antiperspirant and deodorant compositions of the present invention, all of which contain active made in accordance with the anhydrous mixing process of the present invention, may be applied topically to the underarm or other area of the skin in an amount effective to treat or reduce perspiration wetness and/or malodor. The composition is preferably applied in an amount ranging from about 0.1 gram to about 20 grams, more preferably from about 0.1 gram to about 10 grams, even more preferably from about 0.1 gram to about 1 gram, to the underarm or other desired area of the skin. The compositions are preferably applied to the underarm or other area of the skin, one or two times daily, preferably twice daily, to achieve effective antiperspirant and/or malodor control over an extended period.

EXAMPLES

The following nonlimiting examples illustrate specific embodiments of the process of the present invention and the antiperspirant and deodorant compositions containing the zirconium-aluminum salts made in accordance with the process. All exemplified amounts are weight percents based on the total weight of the designated composition, unless otherwise specified.

Example 1

Aluminum chlorhydrate powder (520 grams) and zirconyl oxychloride powder (480 grams) are mixed together in a closed container by gently rolling the container for a period of between about 10 to 15 minutes resulting in a substantially homogeneous mixture of the two powders. The resulting mixture of powders is then removed from the closed container and passed three times through a Retschi ZM1 grinder (available from Retsch GmbH & Co, Haan, West Germany). The resulting mixture is a flowable powder containing zirconium-aluminum salts having the following characteristics:

TABLE 1

| Dry Mix Zirconium-Aluminum Salt | |
| --- | --- |
| % Al | 13.62 |
| % Zr | 14.55 |
| % Cl | 19.69 |
| Al/Zr | 3.22 |
| (Al + Zr)/Cl | 1.19 |
| GPC Peak IV/III area ratio* | 0.92 |

*QPC methodology as defined herein

The resulting zirconium-aluminum salt described in Table 1 is then formulated into an antiperspirant soft solid and its antiperspirant efficacy compared to that of a similar formulation that contains a conventional zirconium-aluminum salt (30B DM CP-5 Active, Westwood Chemical Corp.,) prepared by a prior art aqueous solution method. Although the zirconium-aluminum salts used in the two soft solid formulations are prepared by different methods, each has a GPC Peak IV/II area ratio of about 1.0 and each represents 20% by weight of its respective formulation as calculated on an anhydrous metal salt basis. In short, the two antiperspirant soft solid formulations as described in Table 2 are identical except for the method by which their respective antiperspirant active salts are prepared.

TABLE 2

| Antiperspirant Soft Solids | | |
| --- | --- | --- |
| Ingredient | Example 1.1 | Example 1.2 |
| Dimethicone 350 cst | 43.5% | 43.5% |
| Al Zr salt[1] | — | 26.7% |
| Al Zr salt[2] | 26.7% | — |
| D5 Cyclomethicone | 20.6% | 20.6% |
| Polyethylene beads | 5% | 5% |
| Fumed silica | 3.8% | 3.8% |
| Propylene carbonate | 0.4% | 0.4% |

[1]zirconium-aluminum salt made in accordance with the method of the present invention
[2]zirconium-aluminum salt, Westwood DM CP-5

Examples 1.1 and 1.2 are evaluated for clinical antiperspirant efficacy by standard 7-day hot room testing by an outside clinical laboratory. The data from the evaluation shows no statistical difference at 90% confidence in antiperspirant efficacy between the two sample formulations.

Example 2

Zirconyl hydroxy chloride powder (186 grams) is dissolved in water (401 grams). Glycine (115 grams) is then added to the mixture. Substantially all unbound water is then removed from the mixture by evaporation resulting in a solid powder, about 315 grams of which is mixed with aluminum chlorhydrate (685 grams) powder in a closed container to form a substantially homogeneous mixture of the two powders. The powder mix is then subjected to grinding to reduce particle size and produce an impalpable powder. The resulting mixture is a zirconium-aluminum salt in powder form which has the characteristics described below in Table 3.

TABLE 3

| Dry Mix Zirconium-Aluminum Salt | |
| --- | --- |
| % Al | 17.3 |
| % Zr | 10.16 |
| % glycine | 10.8 |
| % Cl | 15.83 |
| Al/Zr | 5.87 |
| (Al + Zr)/Cl | 1.68 |
| GPC Peak IV/II area ratio* | 1.15 |

*GPC methodology as defined herein

The zirconium-aluminum salt described in Table 3 is then formulated into an antiperspirant stick. Its antiperspirant efficacy is similar to or the same as that of other similar formulations that contain conventional zirconium-aluminum salts, e.g., made by known aqueous solution methods.

TABLE 4

| Antiperspirant Wax Stick | |
| --- | --- |
| Ingredient | Example 2 |
| D5 Cyclomethicone | 51.13% |
| Al Zr Glycinate salt[1] (wt% calculated on anhydrous basis) | 20.0% |
| Stearyl alcohol | 11.0% |
| Talc | 11.0% |
| Dimethicone 50 cst | 3.0% |
| Hydrogenated castor oil | 2.9% |
| Perfume | 0.35% |
| Other | <2.0% |

[1]zirconium-aluminum trichlorohydrex glycinate made by the dry mix method herein

Example 3

The zirconium-aluminum salts as described in Examples 1 and 2 that are made in accordance with the anhydrous mixing process herein are also formulated as particulate antiperspirant actives in solid, semi-solid and liquid antiperspirant formulations, in both aqueous and anhydrous formulations. All of the Example 3 compositions provide antiperspirant efficacy the same as or similar to comparable compositions formulated with conventional active made by prior art methods, e.g., aqueous solution methods.

What is claimed is:

1. A process for making antiperspirant active, which process comprises the step of mixing together a zirconium salt and an aluminum salt to form a zirconium-aluminum salt, wherein the mixture of zirconium and aluminum salts is substantially free of unbound water at all times during the process.

2. The process of claim 1 wherein the aluminum salt prior to the mixing step is substantially free of zirconium and wherein the zirconium salt prior to the anhydrous step is substantially free of aluminum.

3. The process of claim 1 wherein the aluminum and zirconium salts are in the form of solid particulates.

4. The process of claim 1 wherein the aluminum and zirconium salts are in the form of suspended solids in a non-aqueous medium.

5. The process of claim 4 wherein the non-aqueous medium contains less than about 1% by weight of unbound water.

6. The process of claim 1 wherein the aluminum and zirconium salts are in the form of dissolved solids in a non-aqueous medium.

7. The process of claim 6 wherein the non-aqueous medium contains less than about 1% by weight of unbound water.

8. The process of claim 1 wherein the zirconium-aluminum salt has a size exclusion chromatography characterized by an area ratio of Peak IV to Peak III of at least 0.5:1.

9. The process of claim 8 wherein the area ratio of Peak IV to Peak III is from about 0.5:1 to about 1.4:1.

10. The process of claim 1 wherein the aluminum salt prior to the mixing step is combined with a neutral amino acid.

11. The process of claim 10 wherein the neutral amino acid is glycine and the resulting zirconium-aluminum salt is zirconium-aluminum glycinate.

12. The process of claim 1 wherein the zirconium salt prior to the mixing step is combined with a neutral amino acid.

13. The process of claim 12 wherein the neutral amino acid is glycine and the resulting zirconium-aluminum salt is zirconium-aluminum glycinate.

14. The process of claim 1 wherein the zirconium-aluminum salt has an aluminum to zirconium atomic ratio of from about 1:1 to about 10:1.

15. The process of claim 14 wherein the zirconium-aluminum salt has an aluminum to zirconium atomic ratio of from about 2:1 to about 8:1.

16. The process of claim 1 wherein the zirconium-aluminum salt is a halogen salt, and wherein the atomic ratio of the zirconium plus aluminum to the halogen is from about 0.9:1 to about 2.1:1.

17. The process of claim 16 wherein the halogen is chlorine.

18. The process of claim 1 wherein the weight ratio of the aluminum plus zirconium to the neutral amino acid is from about 1:1 to about 10:1.

19. The process of claim 18 wherein the neutral amino acid is glycine and the ratio of zirconium to glycine is from about 0.25:1 to about 5:1.

20. Antiperspirant and deodorant compositions comprising the zirconium-aluminum salt made in accordance with the process of claim 1.

21. The antiperspirant and deodorant composition of claim 20 wherein the composition is in solid form.

22. The antiperspirant and deodorant composition of claim 20 wherein the composition is in semi-solid form.

23. The antiperspirant and deodorant composition of claim 20 wherein the composition is in the form of a liquid.

24. The antiperspirant and deodorant composition of claim 20 wherein the composition is anhydrous and the zirconium-aluminum salt is in solid particulate form.

25. The antiperspirant and deodorant composition of claim 20 wherein the composition is anhydrous and the zirconium-aluminum salt is dissolved in a non-aqueous medium.

* * * * *